United States Patent [19]

Canzi et al.

[11] Patent Number: 5,721,363

[45] Date of Patent: Feb. 24, 1998

[54] PROCESS FOR THE PRODUCTION OF HIGHLY PURE MELAMINE

[75] Inventors: Lorenzo Canzi; Aldo Canzi, both of Milan; Gerhard Coufal, Appiano Gentile; Silvano Giacomuzzo, Cassano Magnago; Mario Virardi, Legnano, all of Italy; Martin Müllner, Linz, Austria

[73] Assignee: Agrolinz Melamin GmbH, Linz, Austria

[21] Appl. No.: 570,863

[22] Filed: Dec. 12, 1995

[30] Foreign Application Priority Data

Dec. 23, 1994 [AT] Austria ................. 2392/94

[51] Int. Cl.$^6$ ............... C07D 251/60; C07D 251/62
[52] U.S. Cl. ................................. 544/201; 544/203
[58] Field of Search ........................ 544/201, 203

[56] References Cited

U.S. PATENT DOCUMENTS

| | | | |
|---|---|---|---|
| 3,116,294 | 12/1963 | Marullo et al. | 260/249.7 |
| 3,484,440 | 12/1969 | Kokubo et al. | 260/249.7 |
| 3,637,686 | 1/1972 | Kokubo et al. | 260/249.7 P |
| 4,565,867 | 1/1986 | Thomas et al. | 544/201 |
| 5,514,796 | 5/1996 | Best et al. | 544/201 |
| 5,514,797 | 5/1996 | Best et al. | 544/203 |

FOREIGN PATENT DOCUMENTS

| | | |
|---|---|---|
| 0 612 560 | 8/1994 | European Pat. Off. |
| 46-16987 | 5/1971 | Japan. |
| 800722 | 9/1958 | United Kingdom. |
| 1032326 | 6/1966 | United Kingdom. |
| WO95/01345 | 1/1995 | WIPO. |

OTHER PUBLICATIONS

*Ullmann's Encyclopedia of Industrial Chemistry*, Fifth Edition, vol. A 16, B. Elvers et al., eds. (1990).

*Primary Examiner*—John M. Ford
*Attorney, Agent, or Firm*—Wenderoth, Lind & Ponack

[57] ABSTRACT

Process for the production of highly pure melamine in which an aftertreatment of the melamine is carried out, comprising the steps a) separating off the $NH_3/CO_2$ gas mixture from the liquid melamine, if appropriate b) reducing the $CO_2$ dissolved in the liquid melamine by introducing gaseous ammonia c) allowing the liquid melamine to remain for a mean residence time of 0 to 8 hours at a temperature between 430° C. and the melting point of melamine and an ammonia partial pressure of 50 to 400 bar and d) slow, controlled cooling by lowering the temperature from the temperature present in a), b) respectively c) to 330° to 270° C. at a cooling rate of up to 150° C./min at an ammonia partial pressure of 50 to 400 bar, higher pressures permitting more rapid cooling rates and, vice versa, lower pressures requiring slower cooling rates, whereupon the reaction vessel in any desired sequence is depressurized and cooled to room temperature and highly pure melamine is obtained in powder form.

10 Claims, No Drawings

PROCESS FOR THE PRODUCTION OF HIGHLY PURE MELAMINE

A multiplicity of processes for the production of melamine are already known from the literature. A preferred starting material in this case is urea which is converted to melamine, ammonia and $CO_2$ either at high pressure and non-catalytically or at low pressure and with the use of a catalyst.

While the known high-pressure processes, for instance in accordance with Melamine Chemicals, Montedison or Nissan, in which the melamine is first formed as a liquid, have a lower energy consumption in comparison to low-pressure processes, the melamine contains, if no purification stages are present, impurities such as melam, melem, ammeline, ammelide or ureidomelamine which interfere with some methods for further processing the melamine.

Melamine produced by a high-pressure process is worked up for example according to U.S. Pat. No. 4,565,867 (Melamine Chemicals) by separating off the $CO_2$ and $NH_3$ off-gasses from the liquid melamine, the pressure and temperature being kept to the same values as are present in the reactor, whereupon the liquid melamine is fed to a product cooling unit, depressurized and rapidly cooled or quenched with a liquid medium, for instance liquid, anhydrous ammonia.

According to U.S. Pat. No. 3,116,294 (Montecatini), the $CO_2$ and $NH_3$ off-gases are likewise first separated off, and the liquid melamine is treated in countercurrent with $NH_3$ in order to remove $CO_2$ which is still dissolved, collected in a further reactor and allowed to remain therein for a certain time. Finally, melamine is removed from the second reactor and rapidly cooled by quenching with water or by mixing with cold gases.

However, the purity of melamine which has been produced by one of these processes is insufficient for many applications, for instance in the production of melamine-formaldehyde resins for surface coatings, since, in particular, the melem content is too high.

According to U.S. Pat. No. 3,637,686 (Nissan), the crude melamine melt obtained by thermal decomposition of urea is rapidly cooled to 200° to 270° C. with liquid $NH_3$ or cold $NH_3$ gas and further cooled to 100° to 200° C. in a second step with aqueous $NH_3$ solution. The product must then be recrystallized in order to achieve a satisfactory melamine purity.

The object of the present invention was therefore to find a process which enables the production of highly pure melamine without additional purification stages having a purity of above 99.8% and a melem content of below 100 ppm.

Unexpectedly, it was possible to achieve this object by a process in which liquid melamine is cooled slowly respectively under control in the last stage.

The present invention therefore relates to a process for the production of highly pure melamine starting from a urea conversion carried out under pressure, which comprises, following the conversion reaction, carrying out an after-treatment of the melamine, comprising the steps a) separating off the $NH_3/CO_2$ gas mixture from the liquid melamine, if appropriate b) reducing the $CO_2$ dissolved in the liquid melamine by introducing gaseous ammonia c) allowing the liquid melamine to remain for a mean residence time of 0 to 8 hours at a temperature between 430° C. and the melting point of melamine and an ammonia partial pressure of 50 to 400 bar and d) slow, controlled cooling by lowering the temperature from the temperature present in a), b) respectively c) to 330° to 270° C. at a cooling rate of up to 150° C./min at an ammonia partial pressure of 50 to 400 bar, higher pressures permitting more rapid cooling rates and, vice versa, lower pressures requiring slower cooling rates, whereupon the reaction vessel, in any desired sequence, is depressurized and cooled to room temperature and highly pure melamine is obtained in powder form.

The process according to the invention is suitable for the purification of melamine which is obtained from urea according to one of the known high-pressure processes, such as according to the Melamine Chemical, Montedison or Nissan process, as described, for example, in Ullmann's Encyclopedia of Industrial Chemistry, 5th Edition, vol. A16, pp 174–179. Urea is generally converted in these processes in a temperature range of 370° to 430° C. and at a pressure of about 70 to 250 bar. The resulting melamine is finally obtained as a liquid phase. According to the novel process, in step a) the reaction mixture formed in the reactor comprising the liquid melamine phase and a $CO_2/NH_3$ gas phase is fractionated in a suitable apparatus, for example in a gas separator, or the gas phase is separated off from the liquid phase. The separator is kept at a temperature above the melting point of melamine; preferably the temperature and pressure are about the same as those in the reactor. The $CO_2/NH_3$ gas mixture, which still contains melamine, is taken off overhead and worked up in a known manner for example by introduction into a scrubber, and reused. Following the gas separation, or at the same time, gaseous $NH_3$ can be introduced which reduces the $CO_2$ dissolved in the melamine (step b). The temperature during this is again at a value above the melting point of melamine; preferably the temperature and pressure are about at the same values as those in the reactor. Whether $NH_3$ is introduced, and the duration of the introduction of the gaseous $NH_3$ and the amount of $NH_3$, depend on the desired final value of the $CO_2$ dissolved in the melamine. The ammonia can be introduced either into the gaseous phase or directly into the liquid melamine phase.

In the next step, the liquid melamine is allowed to stand or remain if appropriate for some time in the presence of ammonia. In this case it is also possible to admix other gases, e.g. nitrogen. The mean residence time in this step is 0 to 8 hours, but under some circumstances higher residence times are also possible. Preferably, the residence time is 10 minutes to 4 hours. During this time, an ammonia partial pressure of 50 to 400 bar, preferably 70 to 200 bar is set. The pressure in step (c) can also be set to a higher value than in the reactor. The temperature in this step is at a value between the melting point of melamine and 430° C., preferably between the melting point of melamine and 400° C.

Following step c) or b) or a) there proceeds the slow respectively controlled cooling of the liquid melamine. In this cooling the liquid melamine is cooled from the temperature present in step c) or b) or a) to a temperature of between 270° C. and 330° C., preferably from a temperature of about 370° to a temperature up to about 290° C. at a defined cooling rate. The cooling rate can be up to 150° C./min, preferably up to 100° C./min, particularly preferably up to 40° C./min. The lower limit of the cooling rate is dependent on technical and economic conditions. It can be selected to be as low as desired in accordance with the existing technical and economic conditions. Step d), like the preceding steps, is carried out in the presence of ammonia. The ammonia partial pressure is 50 to 400 bar in this step, preferably about 70 to 200 bar. Again, a higher pressure than in the reactor can also be set.

The cooling rate to be set is a function of the prevailing ammonia partial pressure, higher pressures permitting more rapid cooling rates and, vice versa, lower pressures requiring slower cooling rates. The cooling rate can if appropriate be varied in the range for cooling under control, in which case no constant cooling rate, but a defined cooling program can be set. A defined cooling program is taken to mean various cooling variants in which the cooling rate can assume different values at various temperatures, it also being possible to vary the pressure. For example, at the beginning of step d), a constant temperature can set over a certain time and then cooling can be performed to the desired final temperature value at a cooling rate selected as a function of the pressure. Another possible variant is, for example, an alternation of holding phases, in which the temperature is held for a certain time at the then prevailing temperature, and cooling phases. Slow and more rapid cooling phases in alternating sequence can also be set. The cooling phase can, if desired, also be carried out by simply shutting off the heating and allowing the mixture to stand at room temperature, which achieves a slow, exponential cooling of the liquid melamine to a preset temperature. The cooling program thus has a plurality of different variants and can be adapted to the particular conditions depending on the desired final value of impurities and as a function of the chosen process sequence.

Above the range (d) for cooling slowly respectively under control, ie in particular above the preferred range in which step d) is carried out, that is above about 370° C., cooling can, depending on the particular conditions, such as process sequence or the apparatus available, be performed either slowly, ie at a cooling rate of up to 150° C./min as a function of the prevailing pressure, or else more rapidly. Below the range for cooling under control, ie below 330° to 270° C., the reaction apparatus can be depressurized and melamine can be cooled to room temperature at any cooling rate, whereupon highly pure pulverulent melamine is obtained. However, depending on the technical conditions, cooling can be performed first and then the apparatus can be depressurized.

The steps a) to d) in the novel process can be carried out if appropriate in separate vessels or apparatuses suitable for the particular step.

However, other variants are also possible. Thus, for example, the steps a) and b), and the steps c) and d), respectively, can be carried out together in the same apparatus.

A further possibility is that, following step a), the melamine is transferred to a delay vessel in which the steps b) and c) are carried out and that step d) proceeds in a separate vessel. The combination of step a) to c) in a shared apparatus with subsequent cooling apparatus for step d) is likewise a possible process variant. However, the mode of carrying out the process must be adapted to the particular conditions, ie according to the equipment for urea conversion, the spatial conditions, the time requirement planned for the cooling phase, the residence time and other factors.

The process according to the invention can, as required, be carried out both discontinuously and continuously.

However, the process according to the invention is also suitable, in somewhat modified form, for purifying contaminated melamine which arises from any process known from the prior art and contains contaminants such as ammeline, ammelide, melam, melem or ureidomelamine. It does not necessarily therefore have to be coupled to a melamine plant. Therefore, mother liquor melamine which, for example, arises in melamine recrystallization processes conventional to date can also be purified in this way.

The present invention therefore further relates to a process for the production of highly pure melamine, which comprises bringing contaminated melamine at an ammonia partial pressure of 50 to 400 bar to a temperature which is between the melting point of melamine and 430° C., allowing the liquid melamine to remain in this temperature range for 0 to 8 hours and then carrying out a slow, controlled cooling, the temperature being decreased to 330° to 270° C. at a cooling rate of up to 150° C./min at an ammonia partial pressure of 50 to 400 bar, higher pressures permitting more rapid cooling rates and, vice versa, lower pressures requiring slower cooling rates, whereupon, in any desired sequence, the reaction vessel is depressurized, cooled to room temperature and highly pure melamine is obtained in powder form.

By means of the process according to the invention, melamine is obtained at a purity of up to over 99.8%, so that further purification steps such as recrystallization are no longer necessary. The content of the individual contaminants, in particular melem, can be kept so low in this case that these compounds do not interfere with any type of further processing of the melamine.

EXAMPLES 1 TO 5 x g of liquid melamine, obtained by conversion of urea on an industrial scale at 375° C. and 70 to 75 bar were introduced into a vessel. A sample was taken therefrom and rapidly cooled and the initial content of contaminants was determined. After separating off the $NH_3/CO_2$ off-gases (step a), the liquid melamine was treated with $NH_3$ for about 15 minutes at 370° C. and 85 bar (step b).

The liquid melamine was then allowed to remain for about 60 to 90 minutes at 370° C. and an ammonia pressure of 85 bar (step c), and the liquid melamine was allowed to cool exponentially to 280° C. by switching off the heating, so that a cooling rate <1° C./min was achieved (step d). The reaction vessel was then depressurized and slowly cooled to room temperature.

The particular amount of melamine, the initial content of the impurities ammeline (AN), ammelide (AD), melem (ME), melam (MA) and ureidomelamine (UM) and the content of the contaminants after the steps a)+b)+c)+d) (final) can be seen in Table 1.

TABLE 1

|  | Melamine (g) | AN (ppm) | AD (ppm) | ME (ppm) | MA (ppm) | UM (ppm) |
|---|---|---|---|---|---|---|
| Example 1 |  |  |  |  |  |  |
| Initial | 1096 | 5700 | 1400 | 17400 | 3000 | 500 |
| Final |  | 100 | <50 | <50 | <300 | <50 |
| Example 2 |  |  |  |  |  |  |
| Initial | 1710 | 4600 | 3000 | 5600 | 1500 | 500 |
| Final |  | 100 | 180 | <50 | <300 | <50 |
| Example 3 |  |  |  |  |  |  |
| Initial | 410 | 4300 | 1600 | 7200 | 2700 | 500 |
| Final |  | 180 | <50 | <50 | <300 | <50 |
| Example 4 |  |  |  |  |  |  |
| Initial | 666 | 4300 | 1000 | 4500 | 1600 | 200 |
| Final |  | 100 | <50 | <50 | <300 | <50 |
| Example 5 |  |  |  |  |  |  |

TABLE 1-continued

| | Melamine (g) | AN (ppm) | AD (ppm) | ME (ppm) | MA (ppm) | UM (ppm) |
|---|---|---|---|---|---|---|
| Initial | 731 | 11400 | 2100 | 8600 | 2300 | 500 |
| Final | | 130 | <50 | <50 | <300 | <50 |

EXAMPLE 6

1700 g of liquid melamine, produced analogously to Examples 1 to 5, were separated off from the $NH_3/CO_2$ off-gases, treated for about 15 min with $NH_3$ at a pressure of 84 bar and allowed to stand for 2 hours at 375° C. and 85 bar.

The heating was then removed, the melamine was allowed to cool slowly to 290° C., depressurized and allowed to cool to room temperature. The final values of contaminants in the melamine were:

| AN: | 100 ppm | ME: | <50 ppm | UM: | <50 ppm |
|---|---|---|---|---|---|
| AD: | <50 ppm | MA: | <300 ppm | | |

EXAMPLE 7

1205 g of liquid melamine, produced analogously to Examples 1 to 5, were separated off from the $NH_3/CO_2$ off-gas, treated with $NH_3$ for about 15 minutes at 85 bar and, without delay time, were allowed to cool to 290° C. after the heating had been switched off. The reaction vessel was then depressurized and cooled to room temperature. The final values of contaminants in the melamine were:

| AN: | 270 ppm | ME: | <200 ppm | UM: | <100 ppm |
|---|---|---|---|---|---|
| AD: | <50 ppm | MA: | 580 ppm | | |

EXAMPLE 8

300 g of melamine containing 8100 ppm of melem and about 65 g of liquid $NH_3$ were heated to 360° C. The ammonia pressure was about 80 bar. The melamine was then allowed to remain under these conditions and then slowly cooled from 360° C. to 330° C. in 28 minutes (cooling rate about 0.8° C./min). The final content of contaminants, as a function of the residence time h, was, after depressurizing the reaction apparatus and cooling to room temperature:

| h | ME ppm | MA ppm | AN ppm | AD ppm |
|---|---|---|---|---|
| 1 | 2250 | <300 | 400 | 50 |
| 2 | 430 | <300 | 320 | <50 |
| 4 | 160 | <300 | 310 | <50 |

EXAMPLE 9

300 g of melamine containing 8100 ppm of melem and the amount of liquid $NH_3$ which is necessary to achieve a defined pressure p were heated to 364° C., allowed to stand for 2 hours under these conditions and cooled from 360° to 330° C. in about 5 minutes (cooling rate 6° C./min).

The content of melem as a function of the particular ammonia pressure set was, after depressurizing the reaction apparatus and cooling to room temperature:

| p (bar) | ME ppm |
|---|---|
| 80 | 1520 |
| 115 | 250 |
| 130 | 160 |
| 151 | 110 |

EXAMPLE 10

300 g of melamine containing 10,000 ppm of melem and 117 g of liquid ammonia were heated to 370° C. The ammonia pressure was 154 bar. The melamine was then allowed to stand under these conditions for 2 hours and cooled from 360° to 330° C. with a cooling rate m.

The melem content after depressurizing the reaction apparatus and cooling to room temperature was, as a function of the cooling time:

| m (°C./min) | ME ppm |
|---|---|
| 7.5 | 210 |
| 0.8 | 100 |

EXAMPLE 11

90 mg of melamine and the amount of ammonia necessary to set an ammonia pressure of 150 bar were heated to 370° C. in an autoclave, allowed to remain for 4 hours under these conditions and then cooled to 290° C. at mean cooling rates of 18° and 36° C./min which were achieved by defined air streams. The reaction vessel was then rapidly cooled to room temperature by immersion in cold water and depressurized. The initial and final melem contents were

| | ME (ppm) |
|---|---|
| Initial | 13000 |
| Final (18° C./min) | 280 |
| Final (36° C./min) | 600 |

EXAMPLE 12

124 mg of melamine and the amount of ammonia necessary to set an ammonia pressure of 200 bar were heated to 370° C. in an autoclave, allowed to remain for 3 hours under these conditions and then cooled to 320° C. at a mean cooling rate of about 100° C./min. The product was then rapidly cooled to room temperature by immersion in cold water and depressurized.

The initial and final melem contents were

| | ME (ppm) |
|---|---|
| Initial | 13000 |
| Final | 250 |

EXAMPLE 13

300 g of melamine containing 10,000 ppm of melem and the amount of ammonia necessary to set an ammonia pressure of 200 bar were heated to 370° C. in an autoclave, allowed to remain for 2 hours under these conditions and then cooled to 320° C. at a cooling rate m and then depressurized. The melem content was, as a function of the cooling rate:

| m (°C./min) | ME ppm |
|---|---|
| 0.9 | <50 |
| 8 | 120 |

We claim:

1. A process for the production of highly pure melamine starting from a urea conversion carried out under pressure wherein liquid melamine and an $NH_3/CO_2$ gas mixture are formed, which comprises, following the conversion reaction, carrying out an after-treatment of the melamine, comprising the steps
   a) optionally separating off the $NH_3/CO_2$ gas mixture from the liquid melamine,
   b) reducing the $CO_2$ dissolved in the liquid melamine by introducing gaseous ammonia
   c) allowing the liquid melamine to remain for a mean residence time of 0 to 8 hours at a temperature between 430° C. and the melting point of melamine and an ammonia partial pressure of 50 to 400 bar and
   d) slow, controlled cooling by lowering the temperature from the temperature present in a), b) respectively c) to 330° to 270° C. at a cooling rate of up to 100° C./min at an ammonia partial pressure of 50 to 400 bar, higher values of said pressure in step c) permitting more rapid cooling rates and, vice versa, lower values of pressure in step c) requiring slower cooling rates, whereupon the reaction vessel in any desired sequence is depressurized and cooled to room temperature and highly pure melamine is obtained in powder form.

2. The process as claimed in claim 1, wherein the residence time in step c) is 10 minutes to 4 hours.

3. The process as claimed in claim 1, wherein the temperature in step c) is between 400° C. and the melting point of melamine.

4. The process as claimed in claim 1, wherein the ammonia partial pressure in step c) is between 70 and 200 bar.

5. The process as claimed in claim 1, wherein the reaction vessel is cooled in step d) from 370° to 290° C. slowly at a controlled cooling rate.

6. The process as claimed in claim 1, wherein the cooling rate in step d) is up to 100° C./min.

7. The process as claimed in claim 1, wherein the cooling rate in step d) is up to 40° C./min.

8. The process as claimed in claim 1, wherein step a) and step b) are carried out simultaneously.

9. The process as claimed in claim 1, wherein step a) and step b) are carried out sequentially.

10. A process for the production of highly pure melamine, which comprises bringing contaminated melamine at an ammonia partial pressure of 50 to 400 bar to a temperature which is between the melting point of melamine and 430° C. where the melamine is liquid, allowing the liquid melamine to remain in this temperature range for 0 to 8 hours and then carrying out a slow, controlled cooling, the temperature being decreased to 330° to 270° C. at a cooling rate of up to 100° C./min at an ammonia partial pressure of 50 to 400 bar, higher values of said pressure permitting more rapid cooling rates and, vice versa, lower values of said pressure requiring slower cooling rates, whereupon, in any desired sequence, the reaction vessel is depressurized and cooled to room temperature and highly pure melamine is obtained in powder form.

* * * * *